(12) United States Patent
Veirman et al.

(10) Patent No.: US 9,938,639 B2
(45) Date of Patent: Apr. 10, 2018

(54) METHOD FOR FORMING A DOPED SILICON INGOT OF UNIFORM RESISTIVITY

(71) Applicant: COMMISSARIAT À L'ENERGIE ATOMIQUE ET AUX ENERGIES ALTERNATIVES, Paris (FR)

(72) Inventors: Jordi Veirman, Poisy (FR); Sébastien Dubois, Scionzier (FR); Nicolas Enjalbert, Burlats (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 213 days.

(21) Appl. No.: 14/437,955

(22) PCT Filed: Oct. 23, 2013

(86) PCT No.: PCT/FR2013/000276
§ 371 (c)(1),
(2) Date: Apr. 23, 2015

(87) PCT Pub. No.: WO2014/064347
PCT Pub. Date: May 1, 2014

(65) Prior Publication Data
US 2015/0284875 A1    Oct. 8, 2015

(30) Foreign Application Priority Data

Oct. 23, 2012 (FR) ........................... 12 02826

(51) Int. Cl.
| | | |
|---|---|---|
| C30B 33/02 | (2006.01) | |
| B28D 1/22 | (2006.01) | |
| G01N 27/04 | (2006.01) | |
| B28D 5/00 | (2006.01) | |

(Continued)

(52) U.S. Cl.
CPC ............... *C30B 33/02* (2013.01); *B28D 1/22* (2013.01); *B28D 5/0011* (2013.01); *C30B 29/06* (2013.01);
(Continued)

(58) Field of Classification Search
CPC ...... B28D 1/22; B28D 5/0005; B28D 5/0011; C30B 29/06; C30B 33/02; G01N 27/041; G01R 31/26
See application file for complete search history.

(56) References Cited

U.S. PATENT DOCUMENTS

| | | |
|---|---|---|
| 5,488,923 A | 2/1996 | Imai et al. |
| 5,876,495 A | 3/1999 | Hiraishi et al. |

(Continued)

FOREIGN PATENT DOCUMENTS

| | | |
|---|---|---|
| DE | 4108394 A1 | 9/1992 |
| EP | 1087041 A1 | 3/2001 |

(Continued)

OTHER PUBLICATIONS

Apr. 28, 2015 International Preliminary Report on Patentability issued in International Patent Application No. PCT/FR2013/000276.

(Continued)

*Primary Examiner* — Timothy V Eley
(74) *Attorney, Agent, or Firm* — Oliff PLC

(57) ABSTRACT

A method for forming a silicon ingot includes the following steps: providing a silicon ingot of variable electrical resistivity and containing interstitial oxygen, determining the interstitial oxygen concentration in different areas of the silicon ingot, calculating the concentration of thermal donors to be created in the different areas to reach a target value of the electrical resistivity, and subjecting the different areas of the silicon ingot to annealing so as to form the (Continued)

thermal donors. The annealing temperature in each area is determined from the thermal donor and interstitial oxygen concentrations of the area and from a predefined annealing time.

12 Claims, 2 Drawing Sheets

(51) Int. Cl.
    *C30B 29/06* (2006.01)
    *F27D 19/00* (2006.01)
    *F27D 21/00* (2006.01)

(52) U.S. Cl.
    CPC ............. *F27D 19/00* (2013.01); *F27D 21/00* (2013.01); *G01N 27/041* (2013.01)

(56) References Cited

U.S. PATENT DOCUMENTS

| | | | |
|---|---|---|---|
| 8,571,812 B2* | 10/2013 | Veirman | G01N 27/041 324/451 |
| 2006/0263967 A1 | 11/2006 | Falster et al. | |
| 2007/0056504 A1 | 3/2007 | Lim | |
| 2009/0210166 A1 | 8/2009 | Nakamura et al. | |
| 2009/0283866 A1 | 11/2009 | Schulze et al. | |
| 2013/0158889 A1 | 6/2013 | Veirman et al. | |
| 2016/0187278 A1* | 6/2016 | Veirman | G01N 21/9501 324/693 |

FOREIGN PATENT DOCUMENTS

| | | |
|---|---|---|
| EP | 1811065 A1 | 7/2007 |
| FR | 1003510 A | 3/1952 |
| JP | H0570279 A | 3/1993 |
| JP | H08133885 A | 5/1996 |
| JP | 2010062466 A | 3/2010 |
| KR | 20050021737 A | 3/2005 |

OTHER PUBLICATIONS

Jan. 8, 2014 International Search Report issued in International Application No. PCT/FR2013/000276.

Kazumi Wada, "Unified Model for Formation Kinetics of Oxygen Thermal Donors in Silicon," Physical Review B, vol. 30, No. 10, Nov. 15, 1984, pp. 5884-5895.

* cited by examiner

METHOD FOR FORMING A DOPED SILICON INGOT OF UNIFORM RESISTIVITY

BACKGROUND OF THE INVENTION

The invention relates to a method for forming a silicon ingot, and more particularly a silicon ingot having a uniform resistivity.

STATE OF THE ART

The Czochralski method is a technique that is commonly used to form single-crystal silicon ingots. It consists in melting a quantity of silicon, called feedstock, in a crucible and in resolidifying the silicon from a seed. The seed, oriented with respect to a crystal axis of the solid silicon, is first dipped in the molten silicon bath. It is then drawn slowly upwards. The solid silicon ingot thus grows progressively feeding on the liquid bath.

The silicon is generally doped to reduce its electrical resistivity. The dopants, such as boron and phosphorus, are incorporated before crystallization, either in the molten feedstock or in the feedstock before the melting step.

With the Czochralski pulling method, the dopants tend to accumulate in the molten silicon bath on account of the segregation phenomenon. The area of the ingot corresponding to the beginning of solidification has a weaker dopant concentration than the area at the end of solidification.

In other words, the dopant concentration in the silicon ingot increases progressively during crystallisation of the latter. This results in a variation of the electrical resistivity over the height of the ingot.

It is however difficult to use the whole of a silicon ingot of variable resistivity. Fabrication of solar cells for example requires a certain resistivity range. It is therefore common practice to scrap one end of the ingot, the one where the resistivity is highest.

To improve the conversion efficiency of solar cells, it has been envisaged to form a silicon ingot having a uniform resistivity over a substantial part of the height of the ingot.

The document US2007/0056504 describes a technique for forming a silicon ingot having a uniform axial resistivity, while keeping the dopant concentration in the molten silicon bath constant. Control of the resistivity is achieved by adding silicon and dopants to the bath at regular intervals.

This technique is tedious as it is necessary, at each addition step, to remove the ingot from the bath and wait until the dopants and the silicon have completely melted.

The dopants are added in the form of powder or of strongly doped silicon wafers. Under these conditions, addition of dopants is accompanied by a contamination of the silicon by other impurities, in particular metallic impurities, which are detrimental for photovoltaic applications. Finally, if a uniform resistivity is not obtained after drawing of the ingot, the latter is scrapped or recycled.

The document KR2005021737 describes another technique to make the resistivity of a silicon ingot uniform, but radially rather than axially. This second technique consists in irradiating the ingot with a strong dose of neutrons, thereby performing doping by transmutation. However, doping by transmutation can only be performed in a nuclear reactor. It is therefore not applicable on a large scale and at low cost.

SUMMARY OF THE INVENTION

It is observed that a requirement exists to provide a simple and economical method for forming a silicon ingot of uniform electrical resistivity and of good metallurgical quality.

This requirement tends to be met by providing a silicon ingot of variable electrical resistivity and containing interstitial oxygen, by determining the interstitial oxygen concentration in different areas of the silicon ingot, by calculating the thermal donor concentration to be created in the different areas to reach a target value of the electrical resistivity and by subjecting the different areas of the silicon ingot to annealing during a predefined time so as to form the thermal donors. The annealing temperature in each area is determined from the thermal donor and interstitial oxygen concentrations of the area and from the annealing time.

The different areas are preferably distributed over the height of the silicon ingot.

The method can further comprise a step of dicing the different areas of the ingot before performing the annealing.

The annealing time is advantageously chosen such that the annealing temperature in the different areas of the silicon ingot is comprised between 400° C. and 500° C.

In a preferred embodiment, the interstitial oxygen concentration is determined by measuring the variation of the electrical resistivity in the different areas of the silicon ingot after formation of thermal donors by a preliminary annealing, the quantity of thermal donors formed by the preliminary annealing being subtracted from the quantity of thermal donors to be created for determining the annealing temperature in each area.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF A PREFERRED EMBODIMENT OF THE INVENTION

Figure 1:
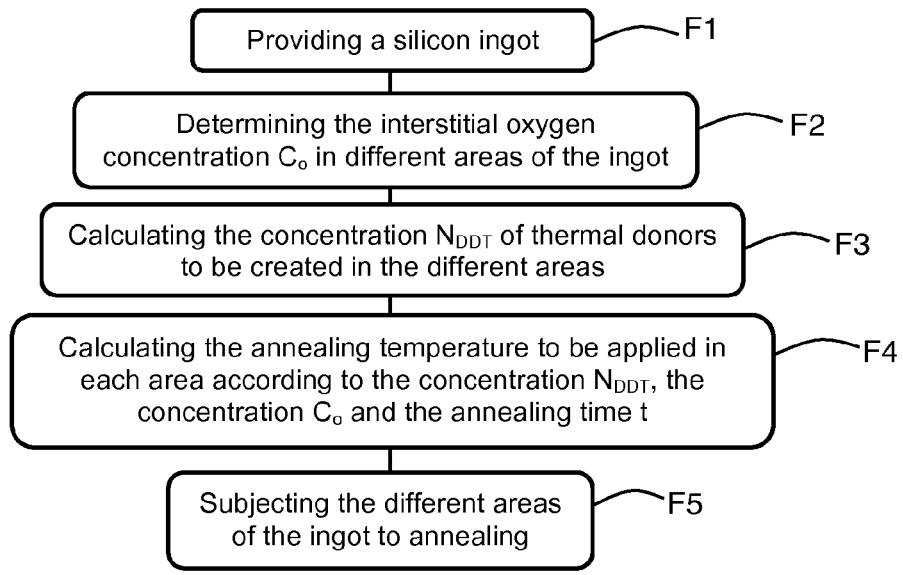
FIG. 1 represents steps of a method for making the electrical resistivity of a crystalline silicon ingot uniform.

The technique proposed in the following consists in correcting the resistivity of a silicon ingot by locally forming thermal donors to tend towards an identical target resistivity in the whole ingot.

The single-crystal silicon obtained by the Czochralski method contains oxygen, typically between $10^{17}$ and $2 \times 10^{18}$ atoms/cm$^3$, and in particular interstitial oxygen (i.e. the oxygen atoms occupy interstitial positions in the crystal lattice).

At a temperature comprised between 350° C. and 550° C., the interstitial oxygen does however form clusters called Double Thermal Donors (DDT). Each thermal donor DDT generates two free electrons, which results in a variation of the electrical resistivity.

The electrical resistivity ρ does in fact vary according to two parameters, the concentration of majority free charge carriers and the mobility μ of these carriers, which depend on the concentration of double thermal donors $N_{DDT}$. Its general expression is the following:

$$\rho(N_{DDT}) = \frac{1}{m(N_{DDT}) \cdot q \cdot \mu(N_{DDT})}, \quad (1)$$

q being the elementary charge (q=1.6×10⁻¹⁹ C).

In a p-doped silicon, the number of majority free charge carriers (holes) is defined by the quantity of dopant impurities of acceptor type implanted in the silicon, for example boron atoms (B). We then have: m=[B].

In an n-type silicon on the other hand, the number of free charge carriers (electrons) is defined by the quantity of dopant impurities of donor type, for example phosphorus atoms (P). We then have: m=[P].

After the heat treatment, each thermal donor releases two electrons ("double" nature of the thermal donors). The free charge carrier concentration is modified in the following manner:

for an n-type silicon:

$$m = [P] + 2 \times N_{DDT} \quad (2), \text{and}$$

for a p-type silicon:

$$m = [B] - 2 \times N_{DDT} \quad (3).$$

Thus, after formation of the thermal donors DDT, the electron concentration is increased by twice the $N_{DDT}$ concentration for an n-type silicon. In a p-type silicon, the hole concentration is reduced by twice the $N_{DDT}$ concentration following rebalancing of the charges.

The mobility μ represents the ability of the charge carriers to be displaced in a material due to the action of an electric field. The mobility of the electrons and of the holes in the silicon depends on the temperature of the material (T') and on the concentration of dopants of donor and/or acceptor type.

Taking the thermal donors DDT (which are dopants of donor type) into account, the mobility can be expressed by the following relation:

$$\mu = \mu_{min} T_n^{\beta 1} + \frac{(\mu_{max} - \mu_{min}) T_n^{\beta 2}}{1 + \left(\frac{N_{A/D} + 4 \times N_{DDT}}{N_{ref} T_n^{\beta 3}}\right)^{\alpha T_n^{\beta 4}}}. \quad (4)$$

$T_n$ is the temperature of the silicon normalized with respect to the ambient temperature ($T_n$=T'/300). $N_{A/D}$ is the concentration of ionized acceptor dopant impurities $N_A$ and/or donor dopant impurities $N_D$ (for example boron and phosphorus). The parameters $\mu_{max}$, $\mu_{min}$, $N_{ref}$, α, β1, β2, β3, β4 are given in the table below for the two types of charge carriers in the silicon.

| Type of carriers | $\mu_{max}$ (cm²·V⁻¹·s⁻¹) | $\mu_{min}$ (cm²·V⁻¹·s⁻¹) | $N_{ref}$ (cm⁻³) | α | β1 | β2 | β3 | β4 |
|---|---|---|---|---|---|---|---|---|
| Electrons | 1417 | 60 | 9.64 × 10¹⁸ | 0.664 | −0.57 | −2.33 | 2.4 | −0.146 |
| Holes | 470 | 37.4 | 2.82 × 10¹⁷ | 0.642 | −0.57 | −2.33 | 2.4 | −0.146 |

Relations (1) to (4) above express the dependency relation between the electrical resistivity ρ of the silicon and the concentration of double thermal donors $N_{DDT}$ generated by heat treatment or annealing of the silicon.

It is therefore proposed to put the thermal donor formation phenomenon into application to correct the electrical resistivity of a silicon ingot.

FIG. 1 represents steps F1 to F5 of a method for obtaining a silicon ingot wherein the electrical resistivity is almost uniform.

In a first step F1, a crystalline silicon ingot of variable electrical resistivity is provided. The crystalline silicon ingot has a longitudinal dimension, in other words its height, which is a minimum of about one centimeter and which is able to go up to several meters. This ingot is preferably obtained from a molten silicon bath by means of the Czochralski (Cz single-crystal silicon) pulling method. A silicon ingot, obtained by directional solidification, can also be used. This type of silicon does in fact contain the oxygen necessary for formation of the thermal donors, in the same way as the Cz single-crystal silicon.

In addition to oxygen, the silicon of the ingot can contain dopants, for example boron and/or phosphorus. These dopants are added to the molten silicon feedstock before drawing of the ingot or are initially present in the feedstock, i.e. before the melting step. On completion of the crystallization, the dopants are distributed in unequal manner in the ingot, which gives rise to a large variation of the electrical resistivity, for example by a factor 10.

A silicon ingot crystallized from a charge that is not deliberately doped can also be provided. The variation of the electrical resistivity on the scale of the ingot is then due to residual dopants which were not removed in the silicon purification phase, or to thermal donors formed during the crystallization (the quantity of which is however of no consequence for the rest of the method). The electrical resistivity will be initially high (typically between 100 Ω·cm and 1000 Ω·cm), but subsequent formation of the thermal donors will lead to a decrease of this resistivity by generating free electrons. The operation which consists in adding dopants to the silicon is thus circumvented, thereby limiting contamination of the silicon by carbon or metallic elements.

Step F2 consists in determining the interstitial oxygen concentration in different areas of the silicon ingot. These areas are preferably distributed over the height of the ingot. The height is defined as being the dimension of the ingot along the solidification axis of the silicon. Thus, in this preferred embodiment, a uniform axial electrical resistivity is sought to be obtained.

The interstitial oxygen concentration, hereafter referred to as $C_o$, can be measured over the height of the ingot by Fourier transform infrared spectroscopy (Whole-rod FTIR). This technique enables the absorption of an infrared radiation in the silicon versus the wavelength of this radiation to be measured. The interstitial oxygen does however contribute to this absorption. It is therefore possible to deduce the concentration $C_o$ from the absorption measurement.

A second technique, also based on formation of thermal donors, enables the oxygen concentration $C_o$ in the silicon to be determined. This technique has been described in detail in Patent application FR1003510, for performing oxygen mapping of a silicon wafer. Here it is applied in advantageous manner on the ingot scale.

Figure 2:
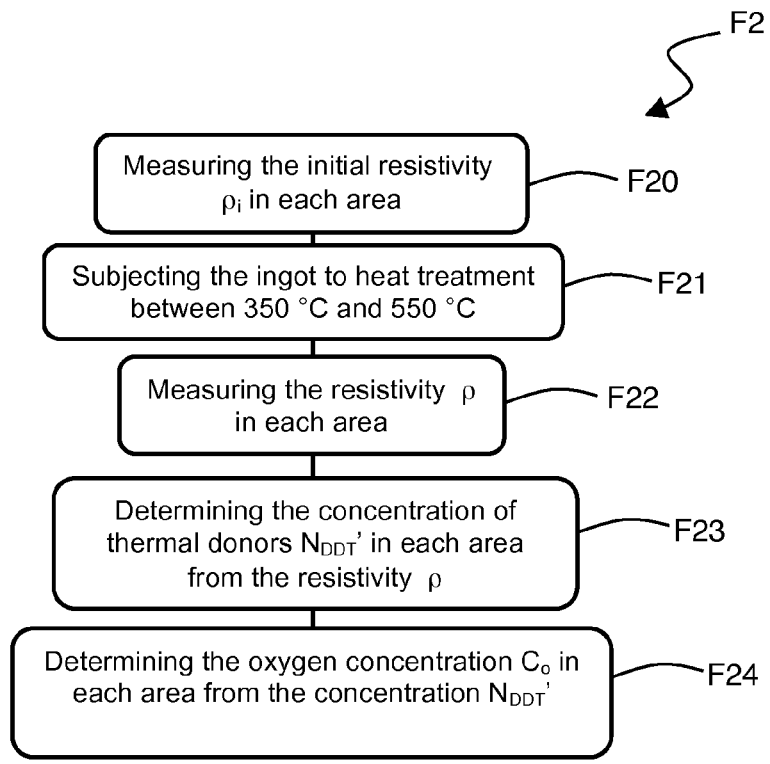
FIG. 2 represents a preferred embodiment of step F2 of FIG. 1.

FIG. 2 represents this preferred embodiment in detail. Step F2 of determining the concentration $C_o$ can be broken down into several sub-steps F20 to F24.

In F20, the initial electrical resistivity at ambient temperature is measured in each area of the silicon ingot.

The silicon ingot is then subjected to a preliminary heat treatment so as to form double thermal donors (DDT) in sub-step F21. Unlike the second annealing designed to make the electrical resistivity of the ingot uniform, the temperature of this first annealing is constant in the ingot. It is preferably comprised between 350° C. and 500° C.

After this annealing, the electrical resistivity is measured at ambient temperature in each of the areas of the ingot (sub-step F22), for example by the four points method (Van der Pauw method).

The variation of the resistivity being attributable to the formation of the thermal donors, the concentration of thermal donors $N_{DDT}{}'$ formed by this preliminary annealing can be deduced therefrom in a sub-step F23. Relation (1) is used for this purpose.

Finally, in step F24, the oxygen concentration $C_o$ in each measurement area is determined from the concentration $N_{DDT}{}'$ and from the preliminary annealing time. Charts giving the concentration $C_o$ for different annealing times and temperatures are advantageously used.

In step F3 of FIG. 1, the concentration of double thermal donors $N_{DDT}$ to be created in each area of the ingot to reach a target value $\rho_T$ of the electrical resistivity is calculated. As the initial resistivity varies in the ingot, the quantity of thermal donors to be generated is not the same depending on the height of the ingot.

This calculation makes use of the foregoing relations (1) to (4) linking the resistivity $\rho$ to the concentration of double thermal donors $N_{DDT}$ (in relation (1) $\rho(N_{DDT})$ is replaced by $\rho T$). It further requires knowing the dopant impurity concentrations $N_A$ and $N_D$ in the different areas of the ingot. If these concentrations are not known (the ingot manufacturer generally establishes the doping profiles over the whole of the ingot), they can be determined in a preliminary step, for example by measuring the initial resistivity in each area.

The resistivity target value $\rho_T$ is chosen according to the applications envisaged for the silicon ingot, for example between 0.5 Ω·cm and 10 Ω·cm for fabrication of solar cells.

On completion of step F3, a value of the interstitial oxygen concentration $C_o$ and a value of the thermal donor concentration $N_{DDT}$ has been obtained for each area of the silicon ingot.

Step F4 consists in calculating the annealing temperature T necessary to obtain the thermal donor concentration $N_{DDT}$ calculated in step F3, for a previously fixed annealing time t. A mathematical model taken from the article ["Unified model for formation kinetics of oxygen thermal donors in silicon"; K. Wade, Physical Review B, Vol. 30, No. 10, 1984] is used for this.

This article describes the formation kinetics of the thermal donors versus the annealing temperature T. The mathematical model is the following:

$$N_{DDT} = A \cdot C_o^3 \cdot n^{-2} \times [1 - \exp(-B \cdot D_i \cdot C_o \cdot t)] \quad (5), \text{ where:}$$

$C_o$ is the interstitial oxygen concentration;
t is the annealing time;
A and B are constants determinable by the person skilled in the art, and in particular they are respectively about $5.6 \times 10^{-6}$ and $5.1 \times 10^{-5}$ and more particularly respectively equal to $5.6 \times 10^{-6}$ and $5.1 \times 10^{5}$;
n is the electron content at the annealing temperature and is equal to:

$$n = 0.5 \times (N_D + \sqrt{N_D^2 + n_i^2})$$

in n-type silicon; or $$n = \frac{n_i^2}{0.5 \times (N_A + \sqrt{N_A^2 + n_i^2})}$$

in p-type silicon;
$n_i$ is the concentration of intrinsic carriers in the silicon, given by the following relation:

$$n_i = 4.43 \times 10^{15} \times T^{3/2} \times \exp\left(-\frac{E_g}{2k_B T}\right),$$

where $k_B$ designates the Boltzmann's constant;
$D_i$ is the interstitial oxygen diffusion coefficient and is written:

$$D_i = 0.17 \times \exp\left(-\frac{2.54}{k_B T}\right);$$

and
Eg is the bandgap energy according to the annealing temperature T (in K):

$$E_g = 1.17 - \frac{4.73 \times 10^{-4} \cdot T^2}{T + 636}.$$

Relation (5) links the thermal donor concentration $N_{DDT}$ to the annealing temperature T, the interstitial oxygen concentration $C_o$ and the annealing time t. The annealing time t, in seconds, can thus be expressed by the following relation:

$$t = -\frac{1}{B \cdot D_i \cdot C_o} \times \ln\left(1 - \frac{N_{DDT} \cdot n^2}{A \cdot C_o^3}\right) \quad (5')$$

The concentrations $C_o$ and $N_{DDT}$ being known, a suitable annealing time t simply has chosen to obtain the annealing temperature T in each measurement area by means of relation (5). The time t is identical for all the areas of the ingot as the areas are subjected to the heat treatment together. It is chosen such that the annealing temperature T in the different areas does not exceed 550° C. Above this temperature, the thermal donors are not formed. On the contrary, they start to break down.

If a temperature T calculated in step F4 exceeds 550° C., the time t is increased so that the temperature values T calculated for the different areas fall into the 350-550° C. temperature range. A value of annealing time t is preferably chosen for the temperatures of the different areas to be comprised between 400° C. and 500° C., a temperature range in which the above-mentioned model is the most precise.

When the oxygen concentration $C_o$ has been determined from the resistivity variation after a preliminary annealing (FIG. 2), thermal donors have already been generated. Calculation of the temperature T of the second annealing must take account of this (otherwise another annealing will have to be performed to eliminate these donors, at a temperature of more than 650=C, ideally for 1 hour). The concentration $N_{DDT}{}'$ of thermal donors generated by the first annealing (determined in step F23) is then subtracted from the concentration $N_{DDT}$ (determined in step F3) for performing calculation of the temperature T. This calculation of the quantity of thermal donors remaining to be created is naturally performed for each measurement area of the ingot.

Once the different temperatures have been calculated, the silicon ingot undergoes the final annealing in a step F5 (FIG. 1) to obtain an almost uniform resistivity. A temperature gradient is applied between the different areas of the ingot so that each area is at its temperature T.

In a preferred embodiment, the different areas of the ingot are diced before the final annealing is performed. The ingot is for example diced into four or five portions, with a height of about 20 to 40 cm. The furnace used for annealing comprises several temperature areas, each portion of the ingot being placed in an area at a certain temperature.

According to a particular embodiment, the silicon ingot provided in step F1 can comprise a radially homogenous oxygen atom concentration $C_o$. The ingot produced by the method will therefore advantageously be homogenous in resistivity, both longitudinally and radially. Furthermore, the method can comprise one or more additional steps to radially make the oxygen atom concentration $C_o$ in the silicon ingot uniform.

The method for correcting the electrical resistivity of an ingot can be applied to the type of doping of the silicon, p-type or n-type. In the case of n-doping, formation of the thermal donors leads to an increase of the number of majority charge carriers, the electrons. The resistivity consequently decreases. In the case of p-doping on the other hand, the resistivity increases as the electrons generated by the thermal donors compensate the holes of the silicon.

A weak (and constant) electrical resistivity can nevertheless be obtained by doping the silicon strongly, before crystallization of the latter. An ingot having a weak and homogenous resistivity can advantageously be used for producing solar cells. In advantageous manner, the method can be implemented to produce a silicon ingot, as well as wafers fabricated by dicing of this ingot, having a resistivity comprised between 1 and 10 Ω·cm.

It is further possible to transform a p-doping into an n-doping by creating more electrons than there are initially holes in the ingot, and by making the resistivity of such an ingot constant.

It should be noted that, in the n-doped silicon at ambient temperature, a part of the thermal donors formed by the annealing are single thermal donors. The latter only generate a single electron instead of two for the double thermal donors.

The quantity of single thermal donors simples can be ignored when the concentration m is less than $5 \times 10^{15}$ cm$^{-3}$. The assumption is then made that all the thermal donors are double and relations (1), (2) and (4) are applicable.

On the other hand, when the concentration m is greater than $5 \times 10^{15}$ cm$^{-3}$, it is preferable to take these single thermal donors into account in calculating the thermal donor concentration (step F3), and then in calculating the annealing temperature (step F4) of each area.

On the one hand, relation (2) giving the free charge carrier concentration m is modified as follows:

$$m = [P] + 2 \times N_{DDT} + N_{SDT} \quad (2')$$

with $N_{SDT}$ the concentration of single thermal donors.

On the other hand, relation (4) of the mobility μ is also modified:

$$\mu = \mu_{min} T_n^{\beta 1} + \frac{(\mu_{max} - \mu_{min}) T_n^{\beta 2}}{1 + \left( \frac{N_{A/D} + 4 \times N_{DDT} + N_{SDT}}{N_{ref} T_n^{\beta 3}} \right)^{\alpha T_n^{\beta 4}}} \quad (4')$$

Calculation of the concentration of thermal donors to be formed when the annealing step is performed henceforth contains two unknowns, the concentration of double thermal donors $N_{DDT}$ and the concentration of single thermal donors $N_{SDT}$ (relation 1=>ρ($N_{DDT}$, $N_{SDT}$)=ρ$_T$). Consequently, a second equation linking the unknowns $N_{DDT}$ and $N_{SDT}$ is necessary to determine the latter.

This second equation is given by the ratio of the concentrations $N_{DDT}$ and $N_{SDT}$ calculated at ambient temperature $T_a$. This ratio is written in the following manner:

$$\frac{N_{DDT}}{N_{SDT}} = 0.5 \times \exp\left( \frac{E_2 - E_F}{k_B T_a} \right) \quad (4'')$$

where $E_2$ is the deep energy level introduced by the thermal donors (at 150 meV under the conduction band), $E_F$ is the Fermi level $$\left( E_F = E_i + \frac{k_B T_a}{q} \times \ln\left( \frac{[P]}{n_i} \right) \right)$$

and $k_B$ is the Boltzmann's constant.

By solving the system of equations (1), (2'), (4') and (4'), both the single thermal donor concentration $N_{SDT}$ and the double thermal donor concentration $N_{DDT}$ are determined. The total concentration $N_{DT} = N_{SDT} + N_{DDT}$ of thermal donors to be formed during annealing to reach the target resistivity value $\beta_T$ is then deduced therefrom.

This total concentration $N_{DT}$ is then used for calculation of the temperatures, in step F4. In other words, in expression (5), the double thermal donor concentration $N_{DDT}$ is replaced by the total concentration $N_{DT}$ calculated beforehand.

Taking the single thermal donors into account as indicated in the foregoing, the difference between the final electrical resistivity of the ingot and the target value of the resistivity that was initially set is minimized. The precision of the method is thereby improved.

The method according to FIG. 1 and its alternative embodiments are preferably implemented over the whole height of the silicon ingot. Scrapping of items is in this way avoided. Unlike the methods of the prior art, it is possible to reuse the ingots which are discarded on completion of solidification, by correcting their resistivity.

Figure 3:
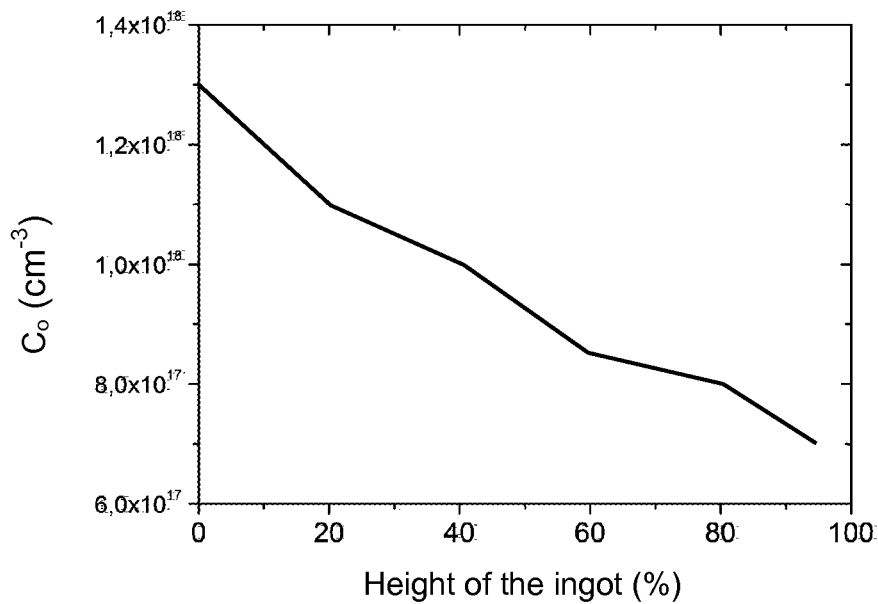
FIG. 3 represents the interstitial oxygen concentration $C_o$ in a single-crystal silicon ingot versus the relative height of the ingot.
Figure 4:
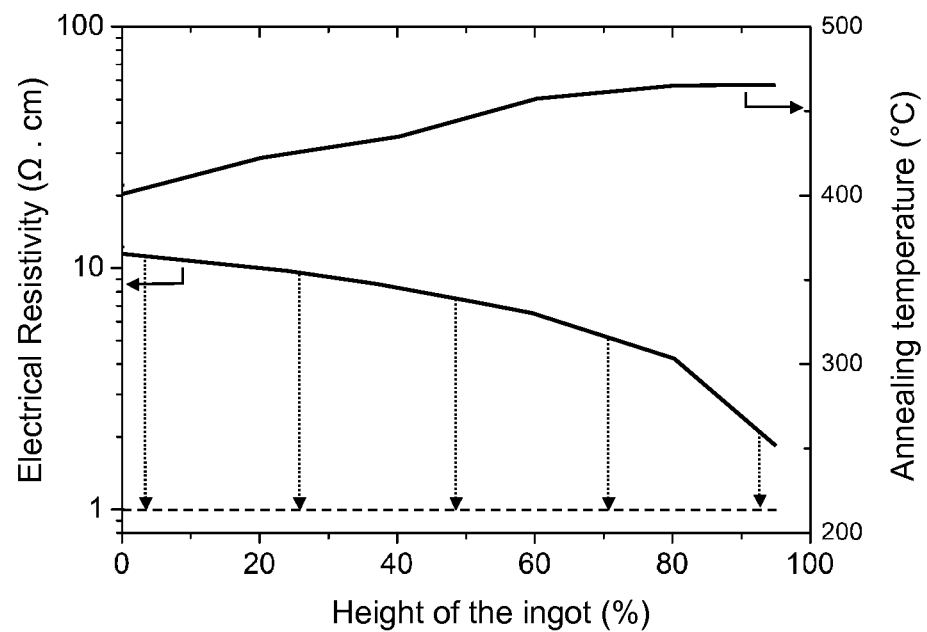
FIG. 4 represents the initial resistivity of the ingot of FIG. 3 and the temperature of the annealing to be applied to the ingot, versus the relative height of the ingot.

FIGS. 3 and 4 illustrate an exemplary embodiment of the method of FIG. 1. The ingot used was crystallized by means of the Czochralski method from a silicon feedstock containing phosphorus ($N_D = [P] = 10^{15}$ cm$^3$). Such an ingot is standard in the photovoltaic industry.

It is desired to obtain an ingot having an axial resistivity that is equal to 1 Ω·cm (ρT=1 Ω·cm) and an annealing time t that is fixed at 1 hour (the shorter the time, the higher the annealing temperature will be).

FIG. 3 represents the oxygen concentration $C_o$ measured over the height of the ingot. The height is calculated here with respect to the end of the ingot corresponding to the beginning of solidification and is expressed in percentage of the total height (relative height).

FIG. 4 represents the initial electrical resistivity of the silicon ingot (on the left-hand y-axis) versus the relative height in the ingot. The target resistivity $\beta_T$ is indicated by a dashed line. It is observed that the electrical resistivity varies between 2 Ω·cm and about 12 Ω·cm.

By means of this plot and of relations (1) to (4), it is possible to calculate the quantity of thermal donors to be created to reduce the resistivity to 1 Ω·cm.

Knowing the thermal donor concentration $N_{DDT}$ and the oxygen concentration $C_o$, the annealing temperature profile T to be applied to the ingot can be determined (relation (5)). This profile is also represented in FIG. 4 (on the right-hand y-axis) in the example of the phosphorus-doped ingot.

The silicon ingot obtained by this method (or the portions of ingot if applicable) is advantageously sliced into silicon wafers for formation of solar cells. The lifetime of the charge carriers in these wafers is high, making them particularly suitable for the advanced architectures of solar cells, such as heterojunction cells.

The lifetime of the charge carriers is high as the silicon is devoid of metallic impurities (iron, nickel, copper, etc.). This is achieved by means of doping performed "in situ", i.e. by forming thermal donors within the material rather than adding dopants in the form of strongly doped wafers or powders.

Naturally, the larger the number of the measurement areas in the ingot, the more precise the oxygen concentration $C_o$ (FIG. 3), thermal donor concentration $N_{DDT}$ and temperature T (FIG. 4) measurements will be over the height of the ingot. On completion of the method of FIG. 1, an almost flat resistivity profile is then obtained at the level of the target resistivity $\rho_T$.

Relations (1) to (4) can be generalized to all types of doping, in particular a silicon called compensated which simultaneously presents both types of dopants, acceptors and donors. The initial free charge carrier concentration is then equal to the difference (in absolute value) of the concentrations of dopant impurities of acceptor type $N_A$ and of donor type $N_D$, whereas the parameter $N_{A/D}$ in expression (3) is equal to the sum of these concentrations ($N_A+N_D$).

If we are in the presence of acceptor dopants of different natures (for example boron and gallium), the concentration $N_A$ is equal to the sum of the concentrations of these dopants (weighted if necessary by their respective ionization coefficients). The same is the case for the concentration $N_D$ in case of plurality of donor dopants (thermal donors excluded).

The invention claimed is:

1. A method for forming a silicon ingot comprising the following steps:
   providing a silicon ingot of variable electrical resistivity and containing interstitial oxygen;
   determining the interstitial oxygen concentration in a plurality of different areas of the silicon ingot;
   calculating a concentration of thermal donors to be created in each area of the plurality of different areas of the silicon ingot so that the electrical resistivity in each area is almost identical;
   determining an annealing temperature for each area of the plurality of different areas of the silicon ingot, the annealing temperature being determined from the interstitial oxygen concentration of each area and from the concentration of thermal donors to be created in each area; and
   subjecting each area of the plurality of different areas of the silicon ingot to annealing so as to form the thermal donors, wherein, for each area of the plurality of different areas, the annealing being defined by the annealing temperature and an annealing time.

2. The method according to claim 1, wherein the plurality of different areas are distributed over the height of the ingot.

3. The method according to claim 1, comprising a dicing step of the plurality of different areas of the silicon ingot.

4. The method according to claim 1, wherein the annealing time is determined according to the following relation:

$$t = -\frac{1}{B \cdot D_i \cdot C_o} \times \ln\left(1 - \frac{N_{DDT} \cdot n^2}{A \cdot C_o^3}\right),$$

where:
$N_{DDT}$ is the calculated thermal donor concentration;
$C_o$ is the interstitial oxygen concentration;
n is the electron content at the annealing temperature;
A and B are constants, wherein A is about $5.6 \times 10^{-6}$ and B is about $5.1 \times 10^{-5}$;
$D_i$ is the interstitial oxygen diffusion coefficient.

5. The method according to claim 4, wherein A is equal to $5.6 \times 10^{-6}$ and B is equal to $5.1 \times 10^{-5}$.

6. The method according to claim 1, wherein the annealing time is chosen such that the annealing temperature in the different areas of the silicon ingot is comprised between 400° C. and 500° C.

7. The method according to claim 1, wherein the interstitial oxygen concentration is determined by measuring a variation of electrical resistivity in the different areas of the silicon ingot after formation of thermal donors by a preliminary annealing, a concentration of thermal donors formed by the preliminary annealing being subtracted from the concentration of thermal donors to be created for determination of the annealing temperature in each area of the plurality of different areas.

8. The method according to claim 1, wherein the interstitial oxygen concentration is determined by Fourier transform infrared spectroscopy.

9. The method according to claim 1, wherein the annealing time is chosen such that the annealing temperature in the different areas of the silicon ingot is comprised between 400° C. and 500° C., and wherein the annealing time is determined according to the following relation:

$$t = -\frac{1}{B \cdot D_i \cdot C_o} \times \ln\left(1 - \frac{N_{DDT} \cdot n^2}{A \cdot C_o^3}\right),$$

where:
$N_{DDT}$ is the calculated thermal donor concentration;
$C_o$ is the interstitial oxygen concentration;
n is the electron content at the annealing temperature;
A and B are constants, wherein A is about $5.6 \times 10^{-6}$ and B is about $5.1 \times 10^{-5}$;
$D_i$ is the interstitial oxygen diffusion coefficient.

10. The method according to claim 9, wherein A is equal to $5.6 \times 10^{-6}$ and B is equal to $5.1 \times 10^{-5}$.

11. A method for forming a silicon ingot comprising the following steps:
   providing a silicon ingot of variable electrical resistivity and containing interstitial oxygen;

determining the interstitial oxygen concentration in a plurality of different areas of the silicon ingot;

calculating a concentration of thermal donors to be created in each area of the plurality of different areas of the silicon ingot to reach a target electrical resistivity value, the target electrical resistivity value being identical for the plurality of different areas of the silicon ingot;

determining an annealing temperature for each area of the plurality of different areas of the silicon ingot, the annealing temperature being determined from the interstitial oxygen concentration of each area and from the concentration of thermal donors to be created in each area; and subjecting each area of the plurality of different areas of the silicon ingot to annealing so as to form the thermal donors for each area of the plurality of different areas, the annealing being defined by the annealing temperature and an annealing time.

12. A method for forming a silicon ingot comprising the following steps:

providing a silicon ingot of variable electrical resistivity and containing interstitial oxygen;

determining the interstitial oxygen concentration in a plurality of different areas of the silicon ingot;

calculating a concentration of thermal donors to be created in each area of the plurality of different areas of the silicon ingot to reach a target electrical resistivity value;

determining an annealing temperature for each area of the plurality of different areas of the silicon ingot, the annealing temperature being determined from the interstitial oxygen concentration of each area and from the concentration of thermal donors to be created in each area; and subjecting each area of the plurality of different areas of the silicon ingot to annealing so as to form the thermal donors for each area of the plurality of different areas, the annealing being defined by the annealing temperature and an annealing time, wherein the interstitial oxygen concentration is determined by measuring a variation of electrical resistivity in the different areas of the silicon ingot after formation of thermal donors by a preliminary annealing, a concentration of thermal donors formed by the preliminary annealing being subtracted from the concentration of thermal donors to be created for determination of the annealing temperature in each area of the plurality of different areas.

\* \* \* \* \*